(12) United States Patent
Krammer et al.

(10) Patent No.: US 11,793,418 B2
(45) Date of Patent: Oct. 24, 2023

(54) SENSOR BELT AND POSITIONING AID FOR ELECTRO-IMPEDANCE TOMOGRAPHY IMAGING IN NEONATES

(71) Applicant: SenTec AG, Therwil (CH)

(72) Inventors: Peter Krammer, Chur (CH); Andreas Waldmann, Chur (CH); Josef Brunner, Chur (CH)

(73) Assignee: SENTEC AG, Therwil (CH)

(*) Notice: Subject to any disclaimer, the term of this patent is extended or adjusted under 35 U.S.C. 154(b) by 576 days.

(21) Appl. No.: 16/349,582

(22) PCT Filed: Nov. 11, 2017

(86) PCT No.: PCT/CH2017/000096
§ 371 (c)(1),
(2) Date: May 13, 2019

(87) PCT Pub. No.: WO2018/085951
PCT Pub. Date: May 17, 2018

(65) Prior Publication Data
US 2019/0274580 A1    Sep. 12, 2019

(30) Foreign Application Priority Data
Nov. 11, 2016    (CH) .................................... 01498/16

(51) Int. Cl.
*A61B 5/0536* (2021.01)
*A61B 5/06* (2006.01)
(Continued)

(52) U.S. Cl.
CPC ............ *A61B 5/0536* (2013.01); *A61B 5/064* (2013.01); *A61B 5/08* (2013.01); *A61B 5/684* (2013.01);
(Continued)

(58) Field of Classification Search
CPC ....... A61B 5/0536; A61B 5/064; A61B 5/085; A61B 5/08; A61B 5/6831; A61B 2576/00;
(Continued)

(56) References Cited

U.S. PATENT DOCUMENTS

| | | | |
|---|---|---|---|
| 5,184,624 A | 2/1993 | Brown et al. | |
| 5,626,146 A | 5/1997 | Barber et al. | |

(Continued)

FOREIGN PATENT DOCUMENTS

| | | |
|---|---|---|
| DE | 10301202 | 1/2004 |
| EP | 2624750 | 8/2013 |

(Continued)

OTHER PUBLICATIONS

Adler and Guardo, Electrical Impedance Tomography: Regularized Imaging and Contrast Detection. IEEE Transactions on Medical Imaging, vol. 15, No. 2 Apr. 1996.

(Continued)

*Primary Examiner* — Sean D Mattson
*Assistant Examiner* — Michael Yiming Fang
(74) *Attorney, Agent, or Firm* — MORRIS O'BRYANT COMPAGNI CANNON, PLLC

(57) ABSTRACT

A system for EIT imaging comprises an electrode array for positioning on a patient and measuring an impedance distribution, a data entry unit and a calculation unit. The electrode array contains a visual aid coupled to the electrode array for visually indicating the position of at least one electrode, the data entry module accepts an entry of data describing the position of the visual aid, and the calculation unit calculates the position of the individual electrodes relative to the patient's body and provides correction for the image creation algorithm. A sensor device for EIT imaging may comprise the electrode array, which is connectable to an (Continued)

EIT imaging system comprising a data entry unit and a calculation unit. An EIT imaging method may employ the system or sensor device.

25 Claims, 6 Drawing Sheets

(51) Int. Cl.
    *A61B 5/08*     (2006.01)
    *A61B 5/00*     (2006.01)

(52) U.S. Cl.
    CPC .......... *A61B 5/6831* (2013.01); *A61B 5/0044* (2013.01); *A61B 5/4848* (2013.01); *A61B 5/74* (2013.01); *A61B 5/7475* (2013.01); *A61B 2503/045* (2013.01); *A61B 2576/00* (2013.01)

(58) Field of Classification Search
    CPC ....... A61B 5/053; A61B 5/068; A61B 5/6801; A61B 5/0033; A61B 5/684; A61B 5/0044; A61B 5/7475
    See application file for complete search history.

(56) References Cited

U.S. PATENT DOCUMENTS

| | | | |
|---|---|---|---|
| 2004/0006279 A1 | 1/2004 | Arad (Abboud) | |
| 2004/0034307 A1 | 2/2004 | Johnson et al. | |
| 2004/0236202 A1 | 11/2004 | Burton | |
| 2004/0260167 A1 | 12/2004 | Leonhardt et al. | |
| 2005/0107833 A1 | 5/2005 | Freeman et al. | |
| 2006/0293609 A1 | 12/2006 | Stahmann et al. | |
| 2009/0084674 A1* | 4/2009 | Holzhacker | A61B 5/417 204/286.1 |
| 2009/0131759 A1 | 5/2009 | Sims et al. | |
| 2010/0168589 A1 | 7/2010 | Banet et al. | |
| 2010/0198101 A1* | 8/2010 | Song | A61N 5/1049 600/547 |
| 2010/0228143 A1 | 9/2010 | Teschner et al. | |
| 2010/0298899 A1 | 11/2010 | Donnelly et al. | |
| 2013/0190577 A1* | 7/2013 | Brunner | A61B 5/1135 600/301 |
| 2014/0143064 A1 | 5/2014 | Tran | |
| 2015/0005608 A1* | 1/2015 | Evans | A61B 5/30 600/382 |
| 2015/0038823 A1* | 2/2015 | Brunner | F24C 15/2035 600/382 |
| 2016/0100791 A1* | 4/2016 | Arad (Abboud) | A61B 5/6831 600/547 |
| 2016/0242673 A1 | 8/2016 | Grychtol et al. | |
| 2019/0038175 A1* | 2/2019 | Woo | A61B 5/0536 |
| 2019/0298219 A1* | 10/2019 | Woo | H05K 1/0283 |

FOREIGN PATENT DOCUMENTS

| | | | |
|---|---|---|---|
| EP | 2624750 A1 * | 8/2013 | .......... A61B 5/6831 |
| EP | 2806792 | 3/2019 | |
| JP | 2013540523 A | 11/2013 | |
| WO | 0033733 | 6/2000 | |
| WO | 2005094369 | 10/2005 | |
| WO | 2006109072 | 10/2006 | |
| WO | 2006121469 | 11/2006 | |
| WO | 2009035965 | 3/2009 | |
| WO | 2009042637 | 4/2009 | |
| WO | WO-2015048917 A1 * | 4/2015 | ............. G09B 23/30 |

OTHER PUBLICATIONS

Brunner et al., Imaging of local lung ventilation under different gravitational conditions with electrical impedance tomography. Acta Astronautica 60 (2007) 281-284.
Costa et al., Electrical impedance tomography. 2009 Wolters Kluwer Health, Lippincott Williams & Wilkins 1070-5295.
French et al., Gravity-dependent phenomena in lung ventilation determined by functional EIT. Physiol. Meas. 17 (1996) A149-A157.
Hahn, et al., Local mechanics of the lung tissue determined by functional EIT. Physiol. Meas. 17 (1996) A159-A166.
Hedenstierna et al., Pulmonary densities during anaesthesia. An experimental study on lung morphology and gas exhange. Eur Respir J. Jan. 27, 1989 528-535.
Schullcke et al., Compensation for large thorax excursions in EIT imaging IOP Publishing Institute of Physics and Engineering in Medicine Physiol. Meas. 37 (2016) 1605-1623.

* cited by examiner a        b

SENSOR BELT AND POSITIONING AID FOR ELECTRO-IMPEDANCE TOMOGRAPHY IMAGING IN NEONATES

TECHNICAL FIELD OF THE INVENTION

This invention relates to a system for electrical impedance tomography imaging (EIT imaging) according to preamble of claim 1, a sensor device for electrical impedance tomography imaging (EIT imaging) according to preamble of claim 12, and an EIT imaging method for measuring an impedance distribution according to preamble of claim 19.

BACKGROUND OF THE INVENTION

Each year 15 million babies are born prematurely and many suffer from respiratory failure due to immaturity of the lung and lack of control of breathing. Although respiratory support, especially mechanical ventilation, can improve their survival, it also causes severe injury to the vulnerable lung resulting in severe and chronic pulmonary morbidity lasting into adulthood. Heterogeneity of lung aeration, resulting in areas of lung over inflation and lung collapse, plays a crucial part in the risk of mortality and morbidity due to respiratory failure. Heterogeneity of lung aeration may pre-exist or may be a complication of therapeutic interventions, for example the inhomogeneous administration of lung surfactant. Heterogeneous distribution of ventilation within the kings cannot be detected by currently available bedside monitoring tools and imaging methods. Thus, an imaging technique for continuous non-invasive bedside monitoring of infants lung function is urgently needed.

Electrical impedance tomography (EIT) is a non-invasive imaging technique used to investigate and measure regional lung ventilation and perfusion (flow of blood) in humans and animals. In contrast to conventional methods, EIT does not require the patient to breathe through a tube or sensor, does not apply ionizing X-rays and can be used for extended periods, say 24 hours or even longer. EIT can be used continuously and is therefore suited for monitoring treatment effects in real time and over time. EIT was first used to monitor respiratory function in 1983 and remains the only bedside method that allows continuous, non-invasive measurements of regional changes in lung volume, blood flow, and cardiac activity. More details of this technique can be found in "Electrical impedance tomography" by Costa E. L., Lima R. G., and Amato M. B. in Curr Opin Crit Care, February 2009, 15 (1), p. 18-24.

In EIT, as disclosed by U.S. Pat. No. 5,626,146, a plurality of electrodes, typically 8 to 32, are arranged on the surface of the body to be examined. A control unit ensures that an electrical signal, for example a current is applied to one or several pairs of electrodes on the skin to establish an electrical field which in turn is measured by the other electrodes. The electrodes used to apply current are called "current injecting electrodes" although one of them might serve as reference ground. Typically, 3 to 10 mA RMS are injected at a frequency ranging from 10 kHz to 300 kHz. With the remaining electrodes, the resulting voltages are measured (forming the "EIT data vector" or the "scan frame") and subsequently used to estimate the distribution of electric impedance within the body. Specific algorithms were developed to convert the set of voltages into images. These conversions are subject to two major challenges: the first challenge is that the mathematical problem is ill-posed and non-linear, the second challenge is inaccurate or plainly false placement of electrodes on the body surface.

To overcome the ill-posed nature of impedance estimation, most EIT imaging algorithms make use of additional assumptions, restrictions or constrains. Typical methods known in the art are the use of a-priori knowledge about the internal structure of the medium and regularization to select a particular solution. Examples of a-priori knowledge include anatomical structures, functions of organs, physical characteristics of tissue like conductivity, blood flow, tuning of heart contraction, and the like.

In the case of respiratory monitoring, a-priori knowledge can be derived, for example, from flow or volume measurements at the airway opening or from an X-ray image of the chest or more preferentially from a CT scan, giving the contour and major structures of a patient's chest. Regularization methods enable to algorithmically decide between competing solutions, producing an image that is a reasonable estimation of the true impedance distribution within the thorax. Anatomical and physiological knowledge as well as physical laws form the basis for regularization methods which are known in the art. For example, abrupt changes in intra-thoracic impedance distribution are usually discarded as non-physiological. Gravity influences the distribution of blood pool and blood flow and therefore the distribution of impedance. Depending on the posture, the disease of the patient and the intra-thoracic location of the impedance distribution, gravity has significant effects on the measured signals. It is known that mechanically ventilated intensive care patients in supine position suffer from regional lung collapse in the dorsal regions of the lungs. Such collapse can lead to or aggravate acute lung injury. Postural change, for example turning the patient to the side or on his front (prone position) may reverse the collapse and can thus have beneficial therapeutic effects.

A three-zone-model may be used to demonstrate the influence of gravity (Hedenstierna G. et al. Pulmonary densities during anaesthesia. An experimental study on lung morphology and gas exchange. Eur Respir J. 1989 June; 2 (6):528.) The three zones of this model are:

Zone 1: open and well aerated alveoli;
Zone 2: unstable alveoli in which their opening and closing is occurring during the respiratory cycle;
Zone 3: collapsed alveoli.

These zones develop for example as a result of patients lying on their back (supine position) or on their stomach (prone position). In healthy subjects, the zones usually disappear in the upright position. The level within the lungs may vary with respect to the gravity vector. But the level usually remains unchanged on a horizontal plane orthogonal to the gravity vector. Ventilation-induced lung injury due to the cyclic opening and closing of lung units is assumed to happen mainly in zone 2. Hypoxemia is caused by the shunting of blood through the non-aerated zone 3. It is a treatment goal to eliminate those two zones in patients.

In mechanically ventilated patients, oxygenation can be improved by changing the body position of the patient. The mechanism behind such improvement is that collapsed lung spaces, described as Zone 3 above, are being opened in the new body position and thus oxygenation of blood is improved. Rotating the body of a mechanically ventilated patient into defined lateral positions to improve lung function is known in the art as disclosed in international application WO2005/094369.

In neonatal patients, the lack of surfactant leads to an enormous increase in the breathing workload and necessitates the administration of external breathing support such as nasal Continuous Positive Airway Pressure nCPAP, intubation and mechanical ventilation or even High Frequency Oscillation Ventilation HFOV. External administration of surfactant is often the treatment of choice to relieve the patient of the high breathing workload. However, surfactant treatment needs to be administered to both lungs homogeneously to prevent lung rupture and economically because surfactant is very expensive. To apply surfactant homogenously to the lungs, regional lung monitoring would be needed. Unfortunately regional lung monitoring is currently unavailable. Some limited lung monitoring, albeit not regional, is possible in intubated and mechanically ventilated by virtue the sensors commonly available as part of the attached ventilator, providing global lung function parameters. However, mechanical ventilation requires intubation, an invasive procedure which should be avoided. In nCPAP and in HFOV, no adequate monitoring is available. Therefore, a monitoring method that provides regional lung data and works in all methods of respiratory support is highly desirable.

Based on above knowledge, it might seem quite obvious to use EIT to monitor the operation of the lung to detect dysfunctions such as a collapse of the lung and the reversal of this collapse. However, in practice collapsed areas are difficult if not impossible to see on EIT images.

To overcome inaccurate placement of electrodes or change of electrode position during breathing and body movement, a number of methods have been described in the literature (by Blott el al. in Phys. Med. Biol 43 (1998) 1731-1739, Jehl et al. in Physiol. Meas. 37 (2016) 893-903, Zhang et al. in The Open Biomedical Engineering Journal, 2013, 7, 109-115). The methods are all using mathematical corrections to compensate for electrode position movement or variations. They were conceived to compensate small changes in electrode position but do fail if the electrode position is plainly wrong. Patent specification U.S. Pat. No. 5,184,624 discloses a method to determine the shape of the body to which the electrodes are attached by using the electrodes to inject current and measure the resulting voltage, using the measured potentials to calculate estimated distances between the corresponding points of current introduction and of potential measurement, and determining estimated electrode positions consistent with these distances, which estimated electrode positions determine the external shape of the body. However, the shape of the body, particularly in neonates, does not carry reliable information about the position of the electrodes relative to the inner organs, for example lung and heart.

For the EIT to yield useful results, the position of the electrodes on the body surface relative to the inner organs needs to be known a priori.

Therefore, a need for improved EIT instrumentation and analysis methods exists, which allow to monitor lung function and to direct patient therapy. In particular long term EIT observation is expected to improve diagnosis and subsequent treatment. For example, due to continuous EIT monitoring, regional lung ventilation and regional lung collapse could be evaluated, the potential for lung injury assessed, and lifesaving treatment options, for example lung recruitment manoeuvres, initiated. Especially intensive care patients could greatly profit from an improved electrical impedance tomography technology and continuous monitoring by EIT. Even more specifically, neonatal patients could greatly profit since conventional imaging methods are not desired because of ionizing radiation. Administration of surfactant therapy could be monitored in nCPAP and HFOV, i.e. even without intubating the patient.

The objective of a previous work was to provide a device and a method that is able to measure and compute reliable EIT difference images. At the core of the invention was the automatic measurement of the patient's position by use of special sensor elements attached to the electrode array as e.g. disclosed in EP 2 624 750 A1. However, attaching a position measurement device to an electrode array does not mean that the patient's position is measurable. If the location of the position measurement device, for example a gravity sensor, is not exactly defined relative to the patient's body, then the position of the patient cannot readily be inferred from the data of the position measurement device. In EP 2 806 792 A1, a method was disclosed to make sure that the electrode arrays are put on the chest in a predictable way by the clinician. This was achieved by integrating the electrode array in a sensor belt assembly and said sensor belt assembly was designed such that it forces the clinician to attach it in a defined position to the patient's chest. A gravity sensor was then connected at a predetermined location and thus permitted to measure the patient's position in real-time and automatically.

In neonatal patients, the method disclosed in EP 2 806 792 A1 cannot be utilized since it consumes too much skin surface. The sensor belt holding the electrode array for neonates needs to be much smaller and thinner than for adults. The following objectives have to be met:

The electrode assembly has to be as small as possible

The electrode assembly has to be extremely skin friendly

The electrode assembly shall not apply any pressure on the baby

The data need to be reliable at all times

The ideal form of a sensor array is a string of electrodes that can be put on the patient's chest in any position. Consequently, the exact position of the electrodes relative to the body of the patient are not known.

It is known that the position of the electrodes relative to the body is of utmost importance to accurately measure and display the results created by EIT. It is also known that the position of the patient relative to gravity is of utmost importance to correctly interpret the results created by EIT. One problem is that these known prerequisites for accurate measurement and interpretation are not compatible with the objectives stated above. In other words, the available technology is not fit for use in neonatal patients.

OBJECTIVE OF THE INVENTION

Therefore, it is an objective of the present invention to provide a device and a method able to identify or enabling identification of the position of the electrode array relative to a patient's body and relative to the gravity vector and consequently able to compute or enabling computation of reliable EIT difference images thereof. It is another objective to provide a device and method that allows to monitor lung function of neonates accurately and in real time.

Furthermore, it is an objective of the present invention to provide a device and a method able to identify or enabling identification of the position of the electrode array relative to a patient's body and preferably also relative to the gravity vector, preferably without employing an acceleration sensor for determining the spatial orientation of the patient's body and the electrode array.

Moreover, it is an objective to simplify EIT methods and at the same time to improve accuracy of the measurement method. Especially it is desired to simplify the positioning of an electrode belt on a patient, in particular on neonates, for the purpose of EIT measurement and imaging. Moreover, it is intended to reduce inaccuracies in EIT images resulting from inaccurately positioned or shifted electrode belts.

For example, a specific objective it is to provide an EIT system which allows random positioning of an EIT belt on a patient (e.g. on a neonate), in particular preferably around a patient's chest. Thus, it is an objective to provide a system which does not require specific electrodes of the belt to occupy predefined positions on the body of the patient, but contrary thereto which takes into account the actual position of the belt and thus of its electrodes.

SUMMARY OF THE INVENTION

Herein is described a system for EIT imaging comprising
an electrode array for positioning on a patient and measuring an impedance distribution,
a data entry module, and
a calculation unit
wherein
the electrode array contains at least one visual aid coupled to the electrode array for the purpose of visually indicating the position of at least a first electrode or electrode pair,
the data entry module accepts an entry of data describing the position of the visual aid,
the calculation unit is adapted to calculate the position of the individual electrodes relative to the patient's body and provide correction for the image creation algorithm so that the electrode position which was assumed during the creation of the reconstruction matrix is mathematically restored.

Thus, above objectives are achieved by providing and using spatial information in order to create reliable EIT images. Spatial information comprises data describing electrode position relative to the patient's body as well as body position and orientation. Standard regularization methods are extended by integrating this spatial information during EIT analysis. Said spatial information may be gathered visually. In addition or alternatively, a sensor for determining the position and spatial orientation of a test person may be coupled to the electrode array and/or a sensor for determining the position of the electrode belt, including the position of individual electrodes, with respect to the patient may be coupled to the electrode array.

Advantageously, in present system, the position of the belt does not need to be set absolutely accurately on a patient, however, as a compromise, the actual position of the belt or at least one or a pair of the electrodes is determined by measuring or reading the position of the visual aid with respect to a specific visible body characteristic, when the patient wears the belt Data describing said position of the visual aid are entered into the data entry module and used by the calculation unit when reconstructing an EIT image from the electro-impedance measurement in order to correct or rather compensate for the belt displacement (i.e. the displacement of the visual aid with regard to the reference body characteristic (i.e. body feature)). By applying the present system quality of EIT images can be improved. Due to the fact that data describing the actual placement of the electrode on the patient's body are measured and entered into the system (if required also repeatedly) renders the application of a loosely applied electrode belt (and therefore displaceable belt) easy and simple. It is not necessary to use fixedly applied electrodes (e.g. electrodes which are glued to the skin, i.e. electrodes whose positions are fixed by gluing them to the skin).

Correction or rather compensation of the belt displacement may be achieved by an algorithm for adapting allocation between the electrodes of the array and electrodes of a virtual anatomic model (in particular, a default allocation between electrodes of the belt array and the model) on account of the measured or read value of displacement. The virtual anatomical model is e.g. embedded in the image creation algorithm. A default allocation setting corresponds for example to a situation where the visual aid is aligned with the characteristic feature of a patient's body (i.e. the reference).

In a preferred embodiment is disclosed a system for EIT imaging, in particular for determining pulmonary function and/or cardiac function, comprising
an electrode array for positioning on a patient and measuring an impedance distribution, with the array being fixed on a belt structure,
a data entry module, and
a calculation unit,
wherein
the electrode array contains at least one visual aid coupled to the electrode array for the purpose of visually indicating the position of at least a first electrode or electrode pair (for this purpose preferably the visual aid is attached on a fixed position on the bell structure),
the visual aid provides a means (e.g. a visual sign such as a line marking as position indicator, optionally including scales), which allows to measure or read the position of the visual aid with respect to a characteristic feature of a patient's body (i.e. a physical reference, e.g. such as the sternum) when the belt structure is worn by a patient,
the data entry module accepts an entry of data describing the position of the visual aid (i.e. the position of the visual aid with respect to the characteristic feature of the patient's body),
the calculation unit is adapted to calculate the position of the individual electrodes relative to the patient's body and provide correction for the image creation algorithm.

Preferably, the visual aid (and consequently the electrode array) comprises means (e.g. scales), which allow to read or measure the position of the visual aid (and consequently the electrode array) with respect to a characteristic feature of a patient's body.

Advantageously, said data describing the position of the visual aid comprise information about the position of the visual aid with respect to the patient. Preferably, said data describing the position of the visual aid comprise information about the position of the visual aid with respect to a characteristic feature of the patient's body. Thus, a predefined feature of the body can be used as a reference. Normally, said data describing the position of the visual aid comprise information about the position of the visual aid at the circumference of a patient, in particular with respect to the inner organs of the patient. The exact position of a visual aid and therefore of one or more individual electrodes of an electrode array may be defined by means of polar coordinates, e.g. by providing a value of an angle with respect to a reference anatomical characteristic, such as e.g. the sternum or rather the dorsal-ventral vector or the middle between the nipples. Thus, advantageously, data describing the (actual) position of the visual aid comprise information about the deviation (such as e.g. the distance or angle) of the visual aid from the characteristic feature of the patient's body (thus, herein also called displacement). In particular, data describing the (actual) position of the visual aid comprise information about the deviation of the visual aid from a desired or predefined position of alignment of the visual aid with the characteristic feature of the patient's body. Said deviation may be expressed e.g. as a distance along the circumference of the patient's body or an angle e.g. measured at or near the central body axis between the circumferential position of the visual aid and the circumferential position of the characteristic feature.

Preferably, for the purpose of providing said correction, based on the data describing the position of the visual aid, a rotational deviation (i.e. e.g. a value for a rotational deviation) of the electrode array from a predefined position is taken into account. The position of the electrode array and therefore the position of the electrodes can be predefined in a virtual anatomical model which is embedded in the calculation unit. Rotational deviation is measured on the chest circumference, for example in a linear dimension along the chest circumference or in an angular dimension measured around a longitudinal body axis.

Advantageously, the calculation unit is adapted to calculate the position of the individual electrodes relative to the patient's body based on the data describing the position of the visual aid.

Advantageously, the data entry module is designed to accept an entry of data describing the position of the patient Preferred is a patient in a lying position. Common lying positions are supine, prone and lateral. The exact position of a lying patient may be defined by means of polar coordinates, e.g. by providing a value of an angle with respect to a reference position.

Advantageously, data describing the position of the patient comprise information about the position of the patient with respect to gravity (or with respect to the gravity vector). Thus, the vector of gravity can be used as a reference for the purpose of describing the position of the patient. Information about the position of the patient preferably comprises information about the orientation of the patient.

For example, said data describing the position of the patient define the position of a lying patient at least as supine position, prone position, right lateral position or left lateral position. Information about the position of a lying patient comprises the orientation of the patient which e.g. is supine, prone, right lateral, left lateral or any other intermediate position between supine and prone.

Preferably, the data entry module accepts a value for the belt displacement, as a means of describing the position of the visual aid with respect to the characteristic feature of the patient's body, and further preferably an entry of chest circumference and an entry of belt size.

Preferably, the system comprises one or more screens, in particular for the purpose of visualizing the position of the patient and the position of the electrode array and for the purpose of presenting the EIT images.

In a preferred embodiment the system is adapted to provide a superposed graphical representation of lung lobe contours (e.g. as comprised in and provided by a virtual anatomical model) including reference to the lobes' spatial orientation and EIT image data provided by the calculation unit after compensation.

In a preferred embodiment further the system is adapted to provide a graphical representation of the position of the electrode array and the visual aid with respect to the patient's body.

In a preferred embodiment the system is able to illustrate on a screen the position of the visual aid on a ring around a graphical representation of the patient, wherein the graphical representation of the patient comprises an indication or information about the position of the patient, preferably about the position of the patient with respect to the gravity vector. Moreover, said visual aid and therefore the position of the electrode array and optionally the position or orientation of the virtual patient on the screen may be amended via the computing unit and/or a touch screen manually in order to display on the screen the actual visually observed position of patient and his electrode array.

Preferably, based on the position of the belt, in particular of at least one electrode or a pair of the electrodes, the position of the other electrodes can be determined, for example by an algorithm, which e.g. takes into account design parameters of the electrodes, such as e.g. number and mutual distance of the electrodes on the belt.

Further is described a sensor device for EIT imaging comprising an electrode array (preferably a belt structure comprising said electrode array) for positioning on a patient and measuring an impedance distribution, which is connectable to an EIT imaging system comprising a data entry module and a calculation unit, wherein the electrode array contains at least one visual aid coupled to the electrode array for the purpose of visually indicating the position of at least a first electrode or electrode pair and prefer-ably wherein the visual aid comprises means (e.g. a line or scales) which allow to determine, i.e. read or measure, the position of the visual aid (and thus the position of the individual electrodes at least of one electrode or of an electrode pair) with respect to a mark or characteristic of the patient's body. Thus, an nurse or medical practitioner may measure or read the deviation (i.e. displacement).

The electrode array can be positioned on a patient in a plurality of ways. When a patient moves the electrode array may slip such that the electrodes move to another position. Even if the electrode array affixed on a belt slides around the chest, the positions of the individual electrodes change even though the belt as a whole still covers the same area of a circumference of a patient's chest. In any of these cases a visual aid coupled to the electrode array can help to determine or read the position of the individual electrodes. Advantageously, said above mentioned means of the visual aid allows to measure or read the deviation (in particular a value for the deviation) of the actual position of the visual aid from a predefined or desired position of alignment of the visual aid and the position of a body mark or characteristic.

For example, said means of the visual aid comprises scales, preferably along a longitudinal edge of the electrode array (i.e. along an edge of the longitudinal extension of the electrode array). Elements of the scales may be lines, arrows and/or other geometrical shapes, which are used to point at body marks or characteristics.

It is further preferred that the visual aid comprises means which allow to align the visual aid (and therefore the electrode array) with distinct marks or characteristic features of the body, such as e.g. the nipples. These, means may be the same means which allow to read ox determine the position of the visual aid (and therefore the position of the electrode array) with respect to a distinct mark on or characteristic of the patient's body.

For example, said means which allow to align the visual aid and/or which allow to read or determine the position of the visual aid comprise scales, preferably along a longitudinal edge of the electrode array (i.e. along an edge of the longitudinal extension of the electrode array).

Normally, the electrodes are arranged in a sequence of spaced apart electrodes. Preferably, the electrode assembly comprises a plurality of at least 8 electrodes, preferably a plurality of at least 16 electrodes.

Advantageously, the electrodes of the electrode array are arranged on or integrated in a belt-like structure and the electrodes are distributed along the longitudinal extension of the belt-like structure. Preferably, the electrodes of the electrode array are fixed to the belt-like structure, optionally they are detachably attached.

Optionally, the data entry module may be attached to the belt like structure.

The data entry module can be a manual data entry module.

Furthermore is described a EIT imaging method comprising positioning and attaching an electrode array on a patient, measuring an impedance distribution,
providing a data entry module with patient specific data, and
calculating an EIT image by means of an image creation algorithm taking into account the measured impedance distribution and patient specific data entries
wherein
the electrode array can be positioned on the patient in a plurality of ways and contains at least one visual aid coupled to the electrode array, which allows for
reading and entering patient specific data comprising information about the position of the visual aid with respect to a characteristic feature of a patient's body, and
calculating the position of the individual electrodes relative to the patient's body and providing correction for the image creation algorithm.

Preferably, for the purpose of providing said correction, based on the data describing the position of the visual aid, a rotational deviation (e.g. a value for a rotational deviation) of the electrode array from a predefined position is taken into account. For example, a value of rotational deviation is a measure of deviation between the visual aid and the characteristic feature of a patient's body.

Advantageously, the position of the individual electrodes relative to the patient's body is calculate by taking into account the position data gathered by means of or with the help of said visual aid.

Advantageously, the described EIT method can be performed on patients in a lying position. This includes the supine, prone or any intermediate position.

Advantageously, the position of the visual aid is determined with respect to the patient, preferably with respect to at least one characteristic body mark (characteristic feature) of the patient.

Advantageously, information about the position of the visual aid comprises the deviation of the visual aid from the characteristic feature of the patient's body. The deviation may be described as e.g. a distance or angle between visual aid and the characteristic feature. More particularly, information about the position of the visual aid comprises the deviation (e.g. distance or angle) of the (actual) position of the visual aid from a desired or predetermined position of alignment with the characteristic feature of the patient's body.

Advantageously, the deviation (e.g. measured as an angle or a distance) of the visual aid from the characteristic feature of the patient's body is determined at the circumference of a patient. In particular, the deviation (e.g. in the form of an angle or a distance) of the actual position of the visual aid from a (desired or predetermined) position of alignment of the visual aid with the characteristic feature of the patient's body is determined at the circumference of a patient.

Advantageously, for the purpose of providing correction for the image creation algorithm the EIT imaging method comprises the step of compensating for a deviation (i.e. belt displacement) of the actual position of a visual aid from a predefined and, therefore, desired position on a patient's body. The desired position, for example, is a position of alignment with a characteristic feature of a patient's body. The predefined position may be defined on the basis of a virtual anatomical model which underlies or is embedded in the image creation algorithm. Advantageously, in present method the deviation (belt displacement) is compensated by allocating the belt electrodes of the array depending on their actual position on the patient's body to their respective and corresponding virtual electrode of a virtual anatomical model.

In a preferred example the position (including the orientation) of the patient is described or determined with respect to the gravity vector and the position of the electrode array is described or determined with respect to at least one characteristic feature of the patient.

In practice, the electrode array and therefore the visual aid is posed at the circumference of a patient, in particular at the circumference of a patient.

It is preferred that the patient specific data comprise information about the position of the patient, preferably the position of a lying patient.

Most preferably, the position of the patient is determined with respect to the gravity vector. The position with respect to gravity is relevant because the functioning of the lung may be influenced by gravity.

BRIEF DESCRIPTION OF THE DRAWINGS

The invention is hereinafter described schematically in the following figures.

Column a: Screen representation of patient position: top shows supine position, middle and bottom show right lateral position;
Column b: Screen representation of sensor belt assembly position with respect to the patient: top and middle show marker on the sternum of the patient, bottom shows marker on the left side of the patient;
Column c: Screen representation of sensor belt assembly position with respect to the patient and to the position of the patient (i.e. combination of the two screen representations in column a and column b): top shows marker on the sternum of a patient in supine position, middle shows marker on the sternum of a patient in right lateral position, bottom shows marker on the left side of a patient in right lateral position.

Figure 7:
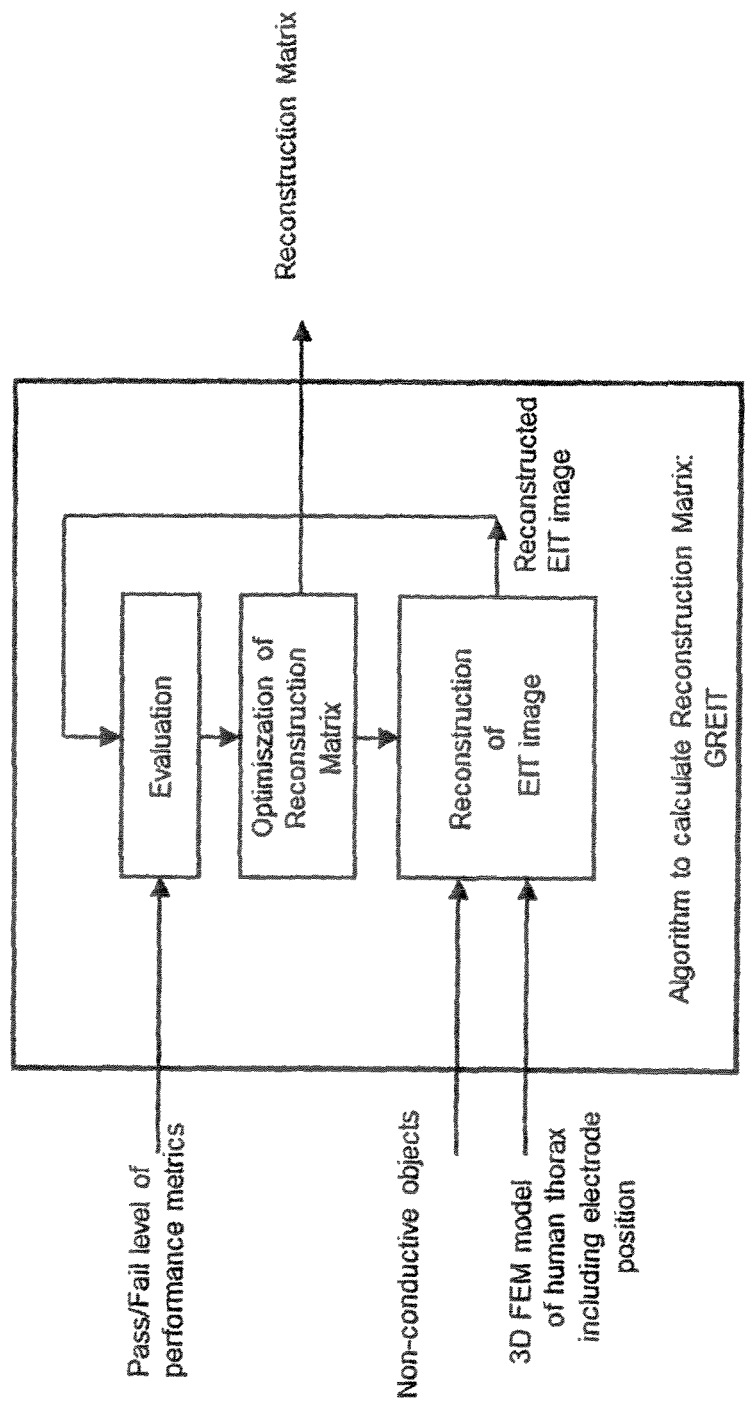

FIG. 7: Schematic representation of an example Reconstruction Matrix of calculation method (GREIT).

Figure 8:
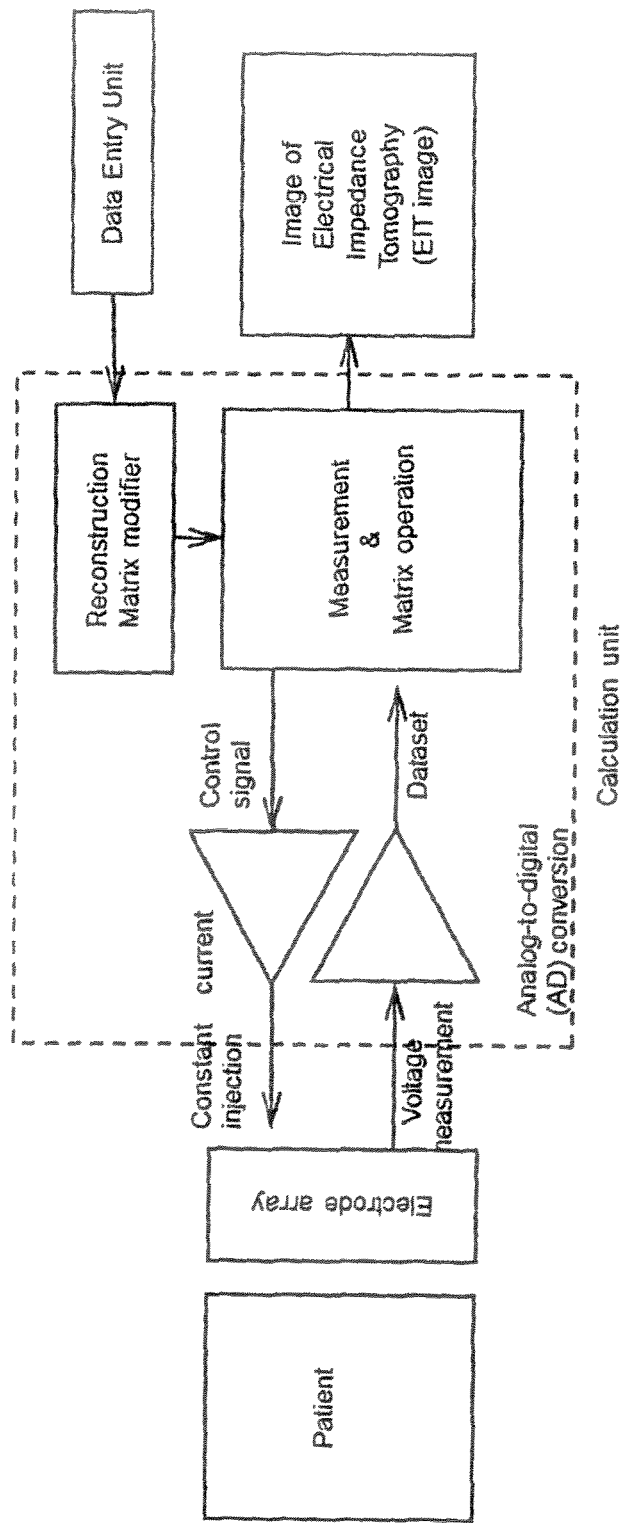

FIG. 8: Real-time image creation procedure.

Figure 9:
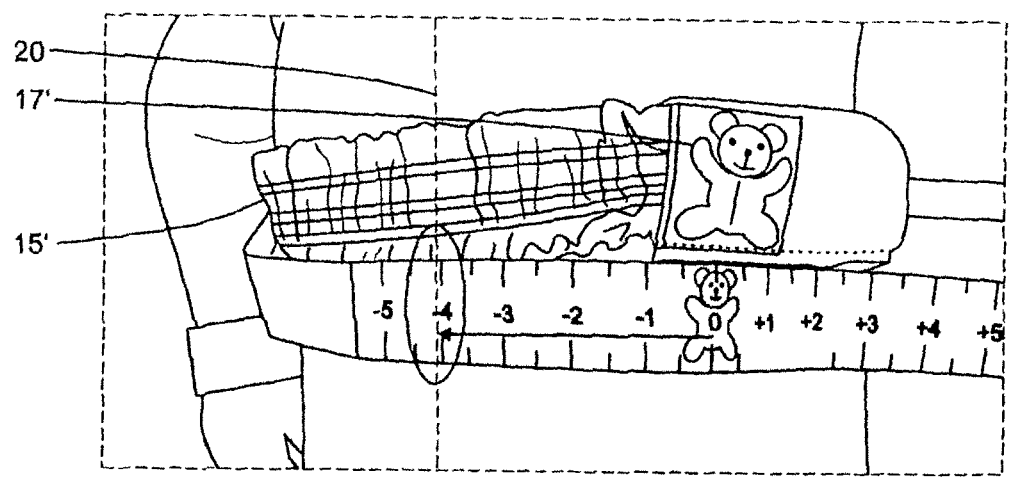

FIG. 9: Schematic drawing of a neonate wearing an electrode belt with visual aid.

Figure 10:
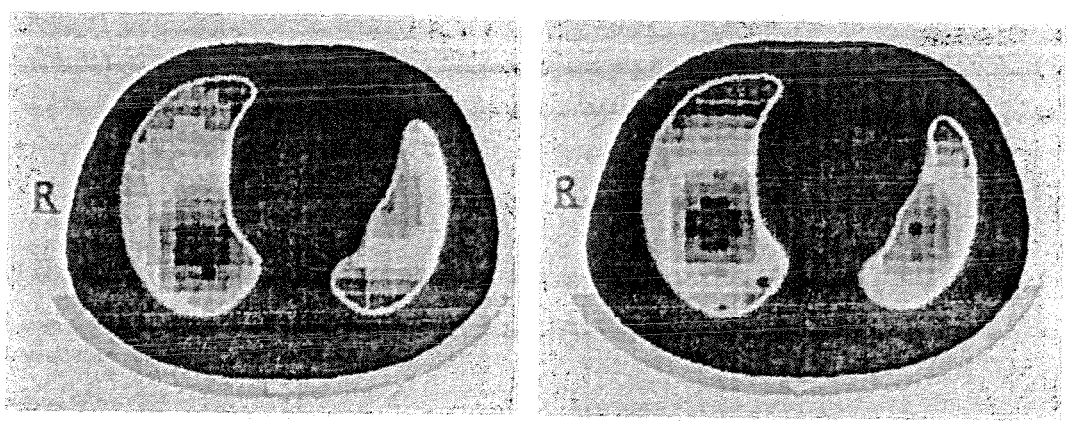

FIG. 10: Charts with EIT image of (a) with correction for the image creation algorithm and (b) without correction for the image creation algorithm.

DETAILED DESCRIPTION OF THE INVENTION

EIT data is obtained by a plurality of electrodes that are placed around the chest of a test person. According to the present invention, the electrodes are preferably mounted on a belt like structure which holds a plurality of electrodes in a geometrically defined position relative to a body part of a test person. In practice an observation plane is selected by placing a belt-like structure assembled with an array of multiple electrodes around a body part. The knowledge of the exact position of the multiple electrodes on the body of a patient is of outmost importance for the purpose of determining accurate electro impedance tomography images and consequent diagnosis.

In FIG. 1a and FIG. 1b the supine position of a patient (especially of a neonate) is represented graphically by the graphic element of the soles 11 of the feet in respective position with respect to a bed 13 (i.e. the toes pointing upward away from the table, thus the patient is in a supine position). The graphic element of a dashed ring 15 surrounding the graphical element of the soles 11 represents an electrode array comprising a plurality of electrodes aligned at spaced intervals. This means that in practice a belt structure carrying the plurality of electrodes is put around the chest of the patient. The patient is lying in supine position on the bed. In order to identify or describe the position of an individual electrode with respect to the patient a visual aid or visual marker 17 is affixed at a fixed position on the electrode array in order to mark at least one specific electrode or electrode pair.

The position of the visual marker 17 and/or the position of the patient may be described by means of a simplified polar coordinate system in a plane, preferably having one coordinate only, i.e. an angle coordinate. A first value of said coordinate (i.e. angle value $\theta_1$) may be used to describe the position of the visual marker 17 and a second value of said coordinate (i.e. angle value $\theta_2$) may be used to describe the position of the patient. The center of the ring 15 (i.e. a point on the longitudinal body axis of a patient) e.g. is defined as the pole of the coordinate system; further, a ray or vector, starting from this point (in the plane of the figure in a direction perpendicular to the longitudinal body axis) and directing parallel to the gravity vector, i.e. vertically upwards, towards the highest position 19 on the electrode array 15, is defined as the polar vector. Position data in this coordinate system comprise a value of an angle $\theta$ between the polar vector and a characteristic vector (thus the angle of a characteristic vector with respect to the position of the polar vector). One characteristic vector e.g. is the vector towards the visual marker 17 of the electrode array 15; another characteristic vector e.g. is a vector pointing to the sternum (i.e. a vector perpendicular to the coronal body plane) herein further called vector of the sternum. The angle which describes the direction of the vector of the sternum with respect to the vector provides information about the position of the patient with respect to gravity. The angle which describes the direction of the vector towards the visual aid with respect to the vector of the sternum provides information about the position of the visual aid with respect to the patient and therewith provides information about the position of the electrode array (or at least of one individual electrode) with respect to the patient or a characteristic feature of the body of the patient.

Figure 1:
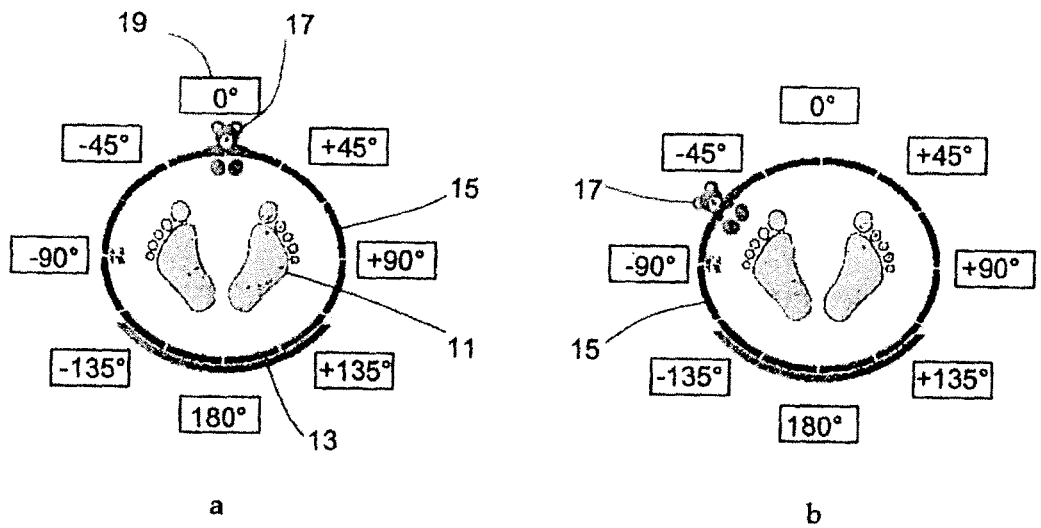
FIG. 1a: Example of implementation on a display unit: Entry of sensor belt assembly with visual marker (bear) at the sternum of the patient.
FIG. 1b: Example of implementation on a display unit: Entry of sensor belt assembly with visual marker (bear) site at the right side of the patient's chest.
Figure 2:
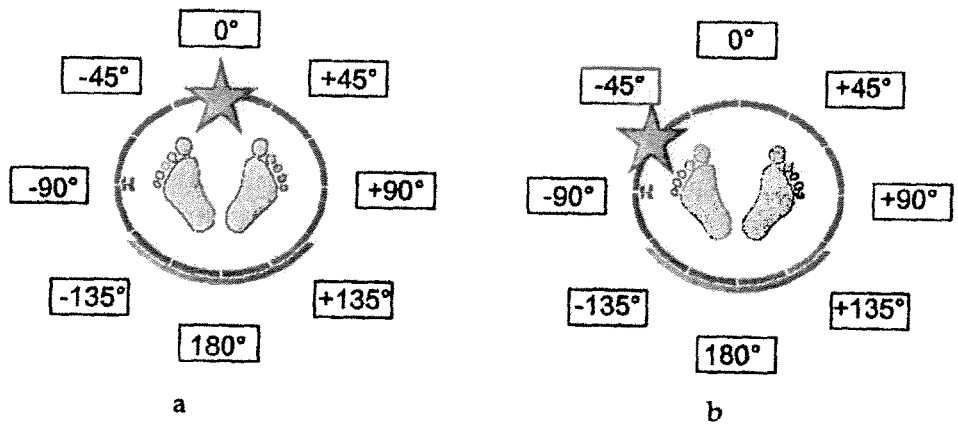
FIG. 2a: Example of implementation on a display unit: Entry of sensor belt assembly with visual marker (star) at the sternum of the patient.
FIG. 2b: Example of implementation on a display unit: Entry of sensor belt assembly with visual marker (star) site at the right side of the patient's chest.

In FIGS. 1 and 2 the planar polar angle coordinate is defined on a scale between 0 and 180 degree, whereby negative values are assigned to positions on the left hand side and positive values are assigned to position the right hand side of an observer situated at the feet of the patient and whereby the central position of the marker above the patient is assigned to the value 0° and the central position of the marker below the patient is assigned to the value 180°. Alternatively, the position of the marker with respect to the patient may be described e.g. by a value between 0 and 360 degree (e.g. measured counterclockwise from the polar axis to the marker position).

In FIGS. 1a and 2a the vector of the sternum of the patient is positioned at a value of 0°, thus the patient is in supine position. Furthermore, the visual aid (bear/star) 17 of the electrode array 15 is positioned at a value of 0° with respect to the polar vector but also with respect to the vector of the sternum which here are at the same position.

In FIGS. 1b and 2b the vector of the sternum of the patient is positioned at a value of 0°, thus the patient is in supine position. Furthermore, the visual aid (bear/star) 17 of the electrode array 15 is positioned at an angle of about −60° with respect to the vector of the sternum. The visual aid (bear)—when considered with respect to the vector of the sternum—is positioned at the frontal right side of the patient's chest. At the same time the patient is in a supine position.

The position of a patient is described with respect to the gravity or the gravity vector (e.g. by means of a first polar coordinate system whose reference is the gravity vector). However, the position of the aid is described with respect to the patient, in particular with respect to a specific characteristic of the patient (e.g. by means of a second polar coordinate system whose reference is the patient, in particular a specific characteristic of the patient, such as e.g. the vector of the sternum).

By means of the herein presented polar coordinate systems, the position of the visual aid with respect to the patient and the position of the patient with respect to gravity can be defined by a value of an angle.

Due to the asymmetry and inhomogeneity of the human chest the exact position of each individual electrode of an electrode assembly is highly relevant for the purpose of analyzing a measured electro impedance distribution and generating representative EIT images.

Figure 3:
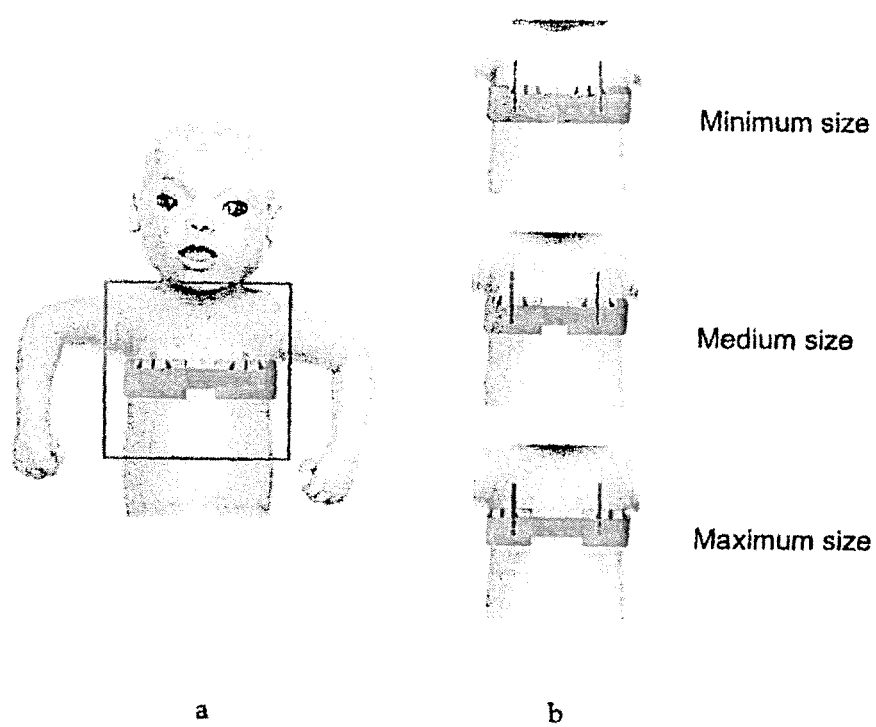
FIG. 3a: Sensor belt assembly with integrated electrodes and 6 markers on the belt to adjust the belt on the body relative to the nipples for medium size of body.
FIG. 3b: Sensor belt assembly with integrated electrodes and 6 markers on the belt to adjust the belt on the body relative to the nipples for minimum size of body (top), medium size of body (middle), maximum size of body (bottom).

FIG. 3a presents a sensor belt assembly with integrated electrodes and 6 markers on the belt. The markers allow adjustment of the belt on the body relative to the nipples. Advantageously the markers of the belt may be brought in line with specific body characteristics such as the nipples of a neonate. Due to a plurality of lines, e.g. as part of a scale, along a longitudinal edge of the belt, the belt can be set on a patient's chest accurately. Moreover, the belt can be adjusted on bodies of different size. FIG. 3b shows chests of neonates of different age or body size.

Figure 4:
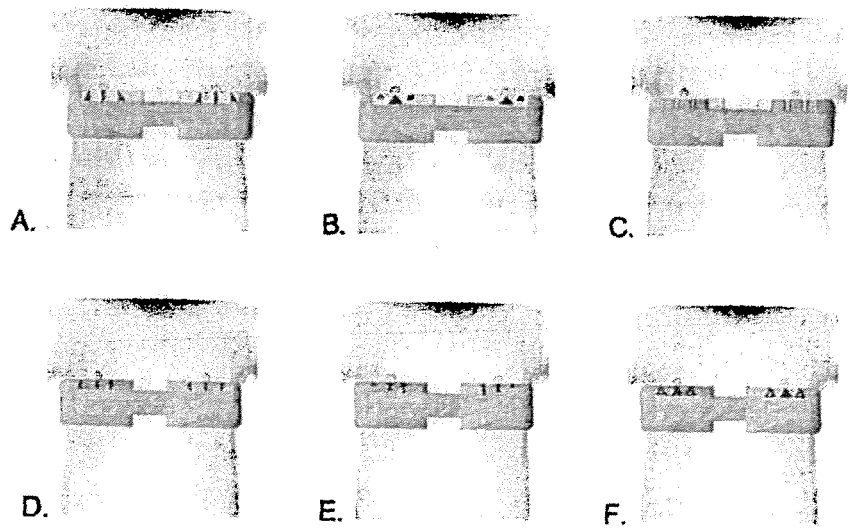
FIG. 4: Different types of visual markers.

In FIG. 4 different examples of visual aids are presented. The elements of the scales may be lines or other geometrical shapes useful to point to specific body marks or characteristics for the purpose of aligning the belt in a defined manner and/or for the purpose of measuring deviation from alignment of belt and body (i.e. measuring deviation of the visual aid from alignment with a specific body mark or characteristic).

An inventive sensor device for EIT imaging comprising an electrode array for measuring an impedance distribution, for example is characterized in that at least one visual aid is uniquely coupled to the electrode array and can be unambiguously assigned to a certain body mark, for example the breast nipples. The assignment of the visual aid to a body mark is entered to a calculation unit which adjusts the internal calculations to match the way the electrode array is mounted on the patient and the patient's body position. The entry of the position of the visual aid relative to a body mark can be done manually or automatically by using an image sensor, for example a camera. The patient's body position may be predetermined, such as e.g. for neonates as lying (e.g. supine or prone), or may be entered manually or automatically as well based on visual observation or measurement by means of a sensor.

Figure 5:
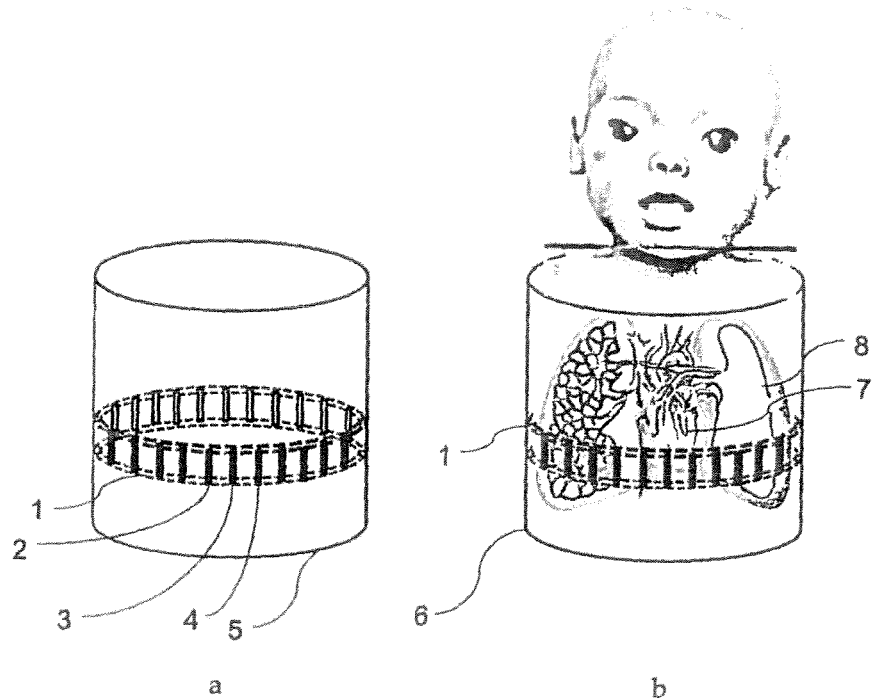
FIG. 5a: Symmetric and homogenous body or object with electrode belt.
FIG. 5b: Asymmetric and inhomogeneous body with electrode belt.

In FIG. 5 a comparison between a homogeneous and symmetric body 5 and a near realistic human chest body is presented. In FIG. 5a a sensor belt assembly 1 with electrodes integrated into the sensor belt assembly, electrode #1 being defined in position 2, electrode #2 in position 3, electrode #3 in position 4 and so on, is attached to body 5 (a cylinder), all around the body. The electrode position does not matter in this case because body 5 is symmetric and homogenous. Irrespective of the position of the individual electrodes of the belt on the body (i.e. on the circumference of the cylinder-shaped body) the EIT image will be the same.

In FIG. 5b the same sensor belt assembly 1 with electrodes integrated into the sensor belt assembly Is attached to body 6. Body 6, however represents the chest of a patient with a sensor belt assembly 1 attached where each electrode (#1, #2 and #3) has a distinct and individual position with respect to the location of the inner organs such as heart 7 and lung 8. Electrode position is of critical importance when reconstructing and analyzing EIT images of a patient because a patient's body 6 is asymmetric and inhomogeneous.

Figure 6:
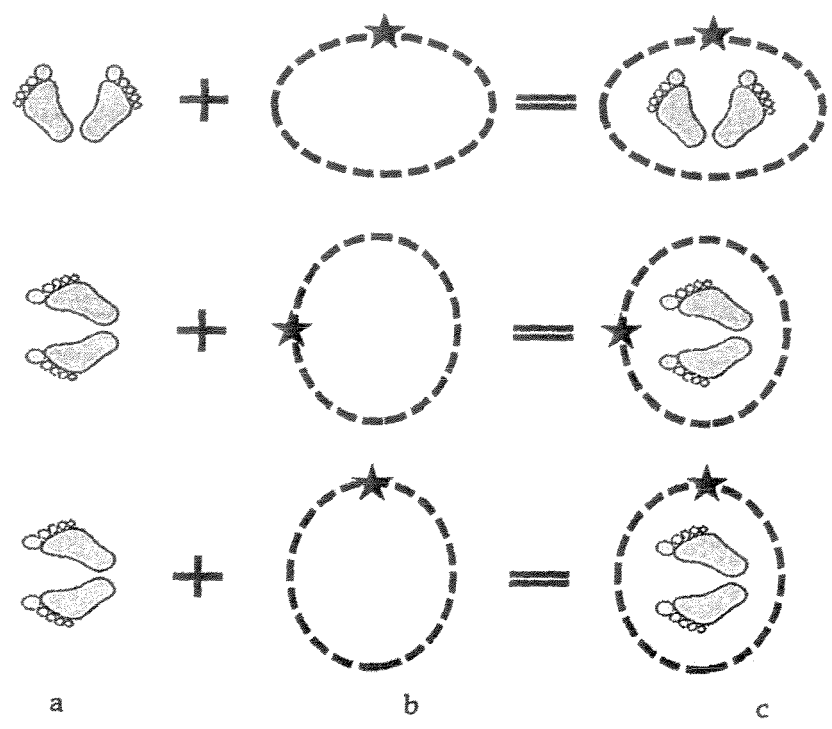
FIG. 6: Screen representations of patient position and/or belt position.

FIG. 6 shows examples of possible screen representations of patient positions and/or belt positions with respect to a patient:

Column a shows a screen representation of patient positions: the first graphic elements (graphic element at the top) presents a supine position of the patient, the second graphic element (graphic element in the middle) and the third graphic element (graphic element at the bottom) present a right lateral position of the patient.

Column b shows a screen representation of sensor belt assembly positions with respect to a patient: the first graphic elements (graphic element at the top) and the second graphic element (graphic element in the middle) present examples where the belt is put on the patient such that the visual marker (star) sits at the sternum of the patient, the third graphic element (graphic element at the bottom) presents an example where the belt is put on the patient such that the visual marker (star) sits on the left side of the patient.

Column c shows a screen representation of sensor belt assembly positions with respect to a patient and with respect to the position of a patient (i.e. combination of the two screen representations in column a and column b): the first graphic element (graphic element at the top) presents an example with a visual marker on the sternum of a patient in supine position, the second graphic element (graphic element in the middle) presents a visual marker on the sternum of a patient in right lateral position, the third graphic element (graphic element at the bottom) presents a visual marker on the left side of a patient in right lateral position.

For the purpose of EIT imaging is relevant on one hand the position of the patient, i.e. the position and orientation of the patient with respect to the gravity vector, and on the other hand the position of the electrodes with respect to the patient, i.e. the position of the electrodes with respect to the inner organs.

FIG. 7 shows a schematic representation of an exemplary reconstruction matrix of calculation method (GREIT). Input is a 3 dimensional finite element model (3D FEM) of the human thorax including the number and exact position of the electrode array. The final reconstruction matrix is obtained by an iterative approach. In a first step, an initial reconstruction matrix is modified to include one or several non-conductive objects. A resulting image is calculated thereof and compared with the expected image. The comparison is evaluated against performance metric and the reconstruction matrix is adapted to better represent the position and size of the non-conductive objects. This procedure takes several minutes until the result converges and has to be done off-line and prior to actual use.

As in FIG. 8 shows, a real-time image creation is done by combining the dataset obtained from voltage measurement, also referred to as voltage frame, with the precalculated reconstruction matrix. For this procedure to work, the electrode position during the actual measurements needs to be identical to the electrode position which was assumed during the calculation of the reconstruction matrix. If it differs, then the reconstruction matrix can be modified to become compatible with the actual electrode position. The data entry module provides a means to inform the calculation unit of the actual electrode position thus making the modification of the reconstruction matrix possible.

In order to give a practical example, FIG. 9 illustrates a baby body (partial view of the chest only) wearing an electrode belt 15' with visual aid 17. The electrodes are not visible, because they are situated on the skin contacting side of the belt. Exemplarily for the purpose of measuring the deviation of the visual aid from the sternum, a measuring tape is employed. Said belt 15' carries a visual aid 17' (depicted bear with central line) which indicates a reference position on the belt 15'. Ideally, the visual aid 17 should be centred at a predefined body mark 20, here e.g. the sternum or also called body midline, because an EIT image creation algorithm predefines and consequently normally would require a respective electrode belt position on a patient when taking EIT measurements. However, in clinical praxis this is not always easily achievable, especially not when involving neonates. Thus, as in this example, there is often a displacement (indicated by the arrows) between the ideally desired position of the visual aid at the body midline and the actual position of the visual aid. With regard to the body midline 20 in FIG. 9, the visual aid is actually displaced to the left body side or in other words the belt is rotated to the left body side, in particular as deductible from the scale depicted in FIG. 9 by about 4 cm. If not accounted for such deviation of the electrode belt interpretation of the EIT measurements is difficult or even impossible.

In FIG. 10 are presented charts of EIT imaging results, in particular showing within two lung lobe contours an image of a distribution of impedance change during a breath cycle (by means of an intensity distribution). This can also be interpreted as a distribution of relative tidal volume. The results presented in FIG. 10(a) were collected without compensation for a belt displacement and the results in FIG. 10(b) were collected with compensation for a belt displacement according to present invention.

Each figure represents a sectional view of the chest with the contours of the modelled lung contours outlined. Depicted within the lung contours are data resulting from EIT measurements in form of an intensity distribution (pixels of different shades). The intensity distribution shows (or rather is a measure of) the distribution of a relative tidal volume or a "relative tidal strain". The tidal volume distribution reflects the change in regional impedance values during a respiratory cycle. During one breath, the lung tissue expands to accommodate the inspired tidal volume.

The "relative tidal strain" is a hypothetical term based on the assumption that impedance changes are caused by tissue expansion or strain. Because these changes are caused by a single breath, they are considered to be the result of a tidal volume impact on the mechanical and thus electrical properties of the surrounding lung tissue—hence the term relative tidal strain.

In FIG. 10(a) EIT results of measurements are shown, which were taken without compensation for the displacement. The results are such that the highest intensity measured in the right lung lobe (in the figure the right side of the patient, who is in supine position, is indicated by R) is located below the centre of the right lung lobe, thus, lower than usually expected, and the highest intensity measured in the left lung lobe is located slightly above the centre of the left lung lobe, thus higher than usually expected. Moreover, low intensity is indicated in the anterior lung lobe area of the right lung lobe while at the same time low intensity is indicated in the posterior lung lobe area of the right lung lobe. If interpreted without considering the shift of the belt, these results are rather unusual. In particular, e.g. it is rather unusual to find low intensity in a posterior lung lobe area.

In FIG. 10(b) EIT results of measurements are shown, which were taken with compensation for the displacement. Actually, measurement is taken of the same patient in the same position, wearing the same belt with visual aid and with the same relative position of belt electrodes and visual aid with regard to the patient's sternum as in FIG. 10(a). However, the results are such that the highest intensity, which indicates the location of the highest tidal volume, is represented in the chart at about the centre of each lung lobe. At the same time low intensity regions mainly can be found at the anterior lung lobe area of each lung lobe. Them are plausible results.

Thus, when comparing the results shown in FIG. 10(a) and in FIG. 10(b) it becomes clear that the compensation of the results can have a huge impact on the interpretability and, thus, the interpretation of the EIT images. Consequently, the here presented manner of compensation is rather useful and important.

As explained hereinabove, the present invention provides a method and system for EIT imaging, which allows for compensation for the displacement of the belt with regard to a predefined belt position, which is simple but effective.

DESCRIPTION OF USE OF THE INVENTION

The present invention can be used to enhance the image quality of EIT devices in stand-alone monitors and in mechanical ventilators and anaesthesia machines. Such improvement can be done e.g. by either creating the enhanced images or by plotting the gravity vector directly on the image, or automatically rotating the image with respect to the gravitational vector thereby providing orientation to the user. A particular use of such improved EIT images is to initiate specific therapies such as recruitment manoeuvres, physiotherapy, or changes in posture and to measure the effectiveness of the therapeutic interventions.

A typical application of the herein presented EIT sensor, EIT system and EIT method is in mechanically ventilated intensive care patients. The herein presented EIT sensor, EIT system and EIT method are particularly useful for neonates whose lung function needs continuous observation. In practice, 15% of mechanically ventilated intensive care patients suffer from acute lung injury and more than 30% of these die. Respective numbers in the age group of neonates are assumed to be even higher due to their particular vulnerability. It is assumed that almost half of these patients could be saved by adequate treatment. Such treatment involves lung recruitment to effectively minimize zones 2 and 3. However, lung recruitment manoeuvres entail risks. Clinicians therefore often use lung recruitments only when lung damage has already become obvious. Unfortunately, this is often too late. With the herein disclosed invention, a care provider would have the means to judge the need and the success of lung recruitment manoeuvres early in disease, save lives, and reduce cost of care.

In another use, the herein presented EIT sensor, EIT system and EIT method can be employed to optimize the body position of a patient, in particular the body position of a neonate, with respect to lung function. This may result e.g. in a reduced need to ventilate mechanically.

In yet another use, the herein presented EIT sensor, EIT system and EIT method can be employed to optimize and monitor the application of surfactant in neonatal patients.

The freedom to apply a sensor belt assembly without constraints and yet creating clinically usable images and movies hinges on the ability to correct for both, the position of the sensor array relative to the inner organs and the body position of the patient relative to gravity. A device that is able to provide the freedom to place an electrode array assembly in any position and still create reliable EIT difference images has not been described previously.

While the invention has been described above with reference to specific embodiments and examples thereof, it is apparent that many changes, modifications, and variations can be made without departing from their inventive concept disclosed herein. Accordingly, it is intended to embrace all such changes, modifications and variations that fall within the spirit and broad scope of the appended claims.

KEY

1 Sensor belt assembly
2 Electrode
3 Electrode
4 Electrode
5 Symmetric and homogenous object
6 Chest of a patient
7 Heart
8 Lung
11 Patient (graphical element of a sole), indicating patient position
13 Bed (graphical element of a cup-like bent line)
15, 15' Electrode array or belt (graphical element of a dashed ring line)

17, 17' Visual marker (graphical element of a bear), indicating individual electrode position
19 Polar angle coordinate
20 Sternum (indicated by dashed line)

The invention claimed is:

1. A system for electrical impedance tomography (EIT) imaging for determining pulmonary function and/or cardiac function, comprising:
a sensor device comprising:
a belt structure comprising an electrode array for positioning on a patient and measuring an impedance distribution, which is configured to be connected to the EIT imaging system comprising a data entry module and a calculation unit;
the electrode array comprising at least one visual aid coupled to the electrode array for visually indicating a position of at least one electrode or an electrode pair;
the at least one visual aid comprising a visual marker affixed at a fixed position on the electrode array to indicate a reference position on the belt structure, and providing a position indicator to indicate a position of the at least one visual aid with respect to a value for belt structure displacement on the patient's body, the position indicator comprising:
either scales along a longitudinal edge of the electrode array or a measuring tape;
the data entry module; and
the calculation unit;
wherein:
the data entry module is adapted to accept an entry of data describing a position of the electrode array, the entry of data comprising a value for belt structure displacement; and
the calculation unit is adapted to calculate a position of the individual electrodes relative to the patient's body and to provide correction for an image creation algorithm, which converts the impedance distribution into images;
wherein the at least one visual aid provides a value for a belt structure rotational deviation from a predefined position:
in a linear dimension along a chest circumference; or
an angular dimension measured around a longitudinal body axis.

2. The system according to claim 1, wherein for the purpose of providing said correction, an electrode array's rotational deviation from the predefined position is taken into account, based on data describing the position of the at least one visual aid.

3. The system according to claim 1, wherein data describing the position of the at least one visual aid comprise information about a deviation of the position of the at least one visual aid from a desired position of alignment with a characteristic feature of the patient's body.

4. The system according to claim 1, wherein, when the at least one visual aid is adapted to be arranged at a circumference of the patient, data describing the position of the at least one visual aid comprise information about the position of the at least one visual aid at the circumference of the patient.

5. The system according to claim 1, wherein the data entry module further accepts an entry of data describing a position of the patient.

6. The system according to claim 5, wherein the data describing the position of the patient comprises information about the position of the patient with respect to gravity or with respect to a gravity vector.

7. The system according to claim 5, wherein the data describing the position of the patient allows the system to define the position of the patient in at least a supine position, a prone position, a right lateral position, or a left lateral position.

8. The system according to claim 1, wherein the system is adapted to provide a superposed graphical representation of: lung lobe contours including reference to their spatial orientation; and EIT image data provided by the calculation unit after the correction.

9. The system according to claim 1, wherein the system is adapted to provide a graphical representation of the position of the electrode array and the at least one visual aid with respect to the patient's body.

10. The system according to claim 1, wherein the system comprises a screen to illustrate the position of the at least one visual aid on a ring around a graphical representation of the patient, wherein the graphical representation of the patient comprises information about a position of the patient.

11. The system according to claim 1, wherein the data entry module accepts an entry of the chest circumference and an entry of belt size.

12. The system according to claim 1, wherein the data entry module is attached to the belt structure.

13. The system according to claim 1, wherein the data entry module is a manual data entry module.

14. A sensor device for electrical impedance tomography (EIT) imaging, comprising:
a belt structure comprising an electrode array for positioning on a patient and measuring an impedance distribution, which is connectable to an EIT imaging system comprising a data entry module for receiving data, and a calculation unit;
wherein:
the electrode array comprises at least one visual aid coupled to the electrode array for visually indicating a position of at least a first electrode or electrode pair;
the at least one visual aid comprises a visual marker affixed at a fixed position on the electrode array indicating a reference position on the belt structure, the at least one visual aid providing a means to read or measure a position of the at least one visual aid with respect to a characteristic feature of the patient's body; and
the data comprises a value for belt displacement;
wherein a position indicator is in the form of either scales along a longitudinal edge of the electrode array or a measuring tape; and
wherein said visual marker provides a value for a rotational deviation of the belt structure from a predefined position;
in a linear dimension along a chest circumference;
or in an angular dimension measured around a longitudinal body axis.

15. The sensor device according to claim 14, wherein said scales provide a value for a deviation of the position of the at least one visual aid from a desired or predetermined position of alignment of the at least one visual aid with the characteristic feature of the patient's body.

16. The sensor device according to claim 14, wherein the at least one visual aid comprises means to align the at least one visual aid with marks or the characteristic features of the patient's body.

17. The sensor device according to claim 14, wherein the scales are arranged along the longitudinal edge of the electrode array.

18. The sensor device according to claim 14, wherein the electrode array comprises a sequence of spaced apart electrodes on or integrated in the belt structure.

19. The sensor device according to claim 18, wherein the spaced apart electrodes are distributed along a longitudinal extension of the belt structure.

20. An electrical impedance tomography (EIT) imaging method, comprising:
positioning and attaching an electrode array on a patient;
measuring an impedance distribution;
providing a data entry module with patient specific data;
calculating an EIT image by means of an image creation algorithm taking into account the measured impedance distribution and the patient specific data;
wherein the electrode array can be positioned on the patient in a plurality of ways and contains at least one visual aid coupled to the electrode array, which allows for:
reading and entering the patient specific data comprising information about a position of the at least one visual aid with respect to a characteristic feature of the patient's body; and
providing a value for a belt rotational deviation from a predefined position of a belt to which the electrode array is attached:
in a linear dimension along a chest circumference; or
in an angular dimension measured around a longitudinal body axis; and
calculating a position of individual electrodes of the electrode array relative to the patient's body and providing correction for the image creation algorithm.

21. The method according to claim 20, wherein for the purpose of providing said correction, based on data describing the position of the at least one visual aid, the belt rotational deviation from the predefined position is taken into account.

22. The method according to claim 20, wherein the information about the position of the at least one visual aid comprises a value for a deviation of the position of the at least one visual aid from a desired position of alignment of the at least one visual aid with the characteristic feature of the patient's body.

23. The method according to claim 20, wherein a deviation of the position of the at least one visual aid from a position of alignment with the characteristic feature of the patient's body is determined at the chest circumference of the patient.

24. The method according to claim 20, wherein the patient specific data further comprise information about a position of the patient.

25. The method according to claim 24, wherein the position of the patient is determined with respect to a gravity vector.

* * * * *